United States Patent
Long et al.

(10) Patent No.: US 10,368,884 B2
(45) Date of Patent: Aug. 6, 2019

(54) IRRIGATION DEVICES, METHODS, AND SYSTEMS

(71) Applicant: Boston Scientific Scimed, Inc., Maple Grove, MN (US)

(72) Inventors: Jerry Long, Jamaica Plain, MA (US); Timothy Harrah, Cambridge, MA (US); Aaron Kirkemo, Gladstone, NJ (US); Brandon Craft, Phoenix, MD (US); Elizabeth Stokley, Baltimore, MD (US); Sebastian Koerner, Berlin (DE); Chad Schneider, Owings Mills, MD (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 139 days.

(21) Appl. No.: 15/402,946

(22) Filed: Jan. 10, 2017

(65) Prior Publication Data
US 2017/0196576 A1     Jul. 13, 2017

Related U.S. Application Data

(60) Provisional application No. 62/277,373, filed on Jan. 11, 2016.

(51) Int. Cl.
*A61B 17/22*     (2006.01)
*A61M 25/00*     (2006.01)
(Continued)

(52) U.S. Cl.
CPC .............. *A61B 17/22* (2013.01); *A61B 5/201* (2013.01); *A61M 3/0295* (2013.01);
(Continued)

(58) Field of Classification Search
CPC ... A61B 17/22; A61B 5/201; A61B 2217/005; A61B 2017/22084; A61B 2017/22067;
(Continued)

(56) References Cited

U.S. PATENT DOCUMENTS

| | | | | |
|---|---|---|---|---|
| 4,945,895 A | * | 8/1990 | Takai | A61B 1/07 600/104 |
| 5,971,968 A | * | 10/1999 | Tu | A61M 25/007 604/103.01 |

(Continued)

OTHER PUBLICATIONS

De, Shuba et al., "Percutaneous Nephrolithotomy Versus Retrograde Intrarenal Surgery: A Systematic Review and Meta-analysis." European Urology 67, 2015, pp. 125-137.
(Continued)

*Primary Examiner* — Bradley J Osinski
(74) *Attorney, Agent, or Firm* — Bookoff, McAndrews, PLLC

(57) ABSTRACT

Irrigation devices, methods, and systems are disclosed. The system comprises a catheter with one or more lumens and an expandable portion. One or more pumps are used to supply a mixture of contrasting and dilating agents in an interior kidney volume and flush a portion of the mixture out of the interior kidney volume. The method comprises placing a catheter into the interior kidney volume through a ureter, occluding a portion of the ureter with a distal end of the catheter, forming an exit port through an exterior kidney surface, flowing the contrasting and dilating agents through the one or more lumens to supply the mixture in the interior kidney volume, and flushing a portion of the mixture out of the exit port.

12 Claims, 7 Drawing Sheets

(51) Int. Cl.
*A61M 3/02* (2006.01)
*A61M 25/10* (2013.01)
*A61B 5/20* (2006.01)
*A61B 6/00* (2006.01)
*A61M 39/02* (2006.01)

(52) U.S. Cl.
CPC ........ *A61M 25/0017* (2013.01); *A61M 25/10* (2013.01); *A61B 6/481* (2013.01); *A61B 6/487* (2013.01); *A61B 2017/22067* (2013.01); *A61B 2017/22079* (2013.01); *A61B 2017/22084* (2013.01); *A61B 2217/005* (2013.01); *A61B 2217/007* (2013.01); *A61M 2039/0276* (2013.01); *A61M 2205/3331* (2013.01); *A61M 2205/3379* (2013.01); *A61M 2210/005* (2013.01); *A61M 2210/1082* (2013.01); *A61M 2210/1085* (2013.01); *A61M 2210/1089* (2013.01)

(58) Field of Classification Search
CPC .............. A61B 2217/007; A61B 6/481; A61B 2017/22079; A61M 3/0295; A61M 25/0017; A61M 2210/1089; A61M 2210/1085; A61M 2210/1082; A61M 2210/005; A61M 2039/0276
See application file for complete search history.

(56) References Cited

U.S. PATENT DOCUMENTS

| | | | |
|---|---|---|---|
| 8,771,287 | B2 | 7/2014 | Wynberg |
| 9,084,847 | B2 | 7/2015 | Klein et al. |
| 2002/0119116 | A1* | 8/2002 | Sahatjian ......... A61B 17/22004 424/78.31 |
| 2009/0281507 | A1* | 11/2009 | Humphreys ....... A61B 17/3421 604/264 |
| 2010/0274231 | A1 | 10/2010 | Pravong et al. |
| 2015/0119795 | A1 | 4/2015 | Germain et al. |

OTHER PUBLICATIONS

Sivalingam, Sri et al., "Percutaneous Nephrolithotomy with Retrograde Nephrostomy Access: A Forgotten Technique Revisited." Journal of Urology, vol. 189, May 2013, pp. 1753-1756.

* cited by examiner

IRRIGATION DEVICES, METHODS, AND SYSTEMS

CROSS-REFERENCE TO RELATED APPLICATIONS

This patent application claims the benefit of priority under 35 U.S.C. § 119 to U.S. Provisional Patent Application No. 62/277,373, filed Jan. 11, 2016, which is herein incorporated by reference in its entirety.

TECHNICAL FIELD

Aspects of the present disclosure generally relate to medical devices and procedures. In particular, some aspects relate to irrigation devices, methods, and systems used in percutaneous nephrolithotomy ("PCNL") procedures.

BACKGROUND

PCNL procedures are used to remove kidney stones from a calyx of a kidney. The prerequisite for most PCNL procedures is the establishment of a satisfactory nephrostomy tract, which can be achieved by a urologist using an antegrade approach (from outside a body into the calyx) or a retrograde approach (from the ureter into the calyx). The antegrade approach is most commonly used; however, the retrograde approach can provide numerous benefits to many patients, such as positional advantages that prevent injury, decreased radiation exposure, optimal calyceal selection, and potentially decrease operative time.

Limited visualization discourages the retrograde approach. Fluoroscopy may overcome this limitation, but it only provides a two dimension view of the kidney, making it difficult for the surgeon to determine exactly which calyx has been accessed by the nephrostomy tract. Irrigation techniques are often used in PCNL procedures to flush each calyx. Some of these techniques utilize fluids that can enhance the images by provided by fluoroscopy. Yet, because the kidney naturally drains out into the ureter, these techniques have heretofore proven incompatible with the retrograde approach.

Further improvements are required to make the benefits of the retrograde approach more accessible.

SUMMARY

Aspects of the present disclosure relate to irrigation devices, methods, and systems. Numerous aspects of the present disclosure are now described.

One aspect is an irrigation system. The system may comprise a catheter including a first lumen, a second lumen, and an expandable portion. A first pump may flow a dilating agent from a first reservoir and through the first lumen, whereas a second pump may flow a contrasting agent from a second reservoir and through the second lumen. The first and second pumps may be operable to supply a mixture of the contrasting and dilating agents in an interior kidney volume, and flush a portion of the mixture out of an exit port formed in the interior kidney volume.

Aspects of this system may additionally and/or alternatively include one or more of the features set forth below. The catheter may have an inner diameter, and the first and second lumens may be defined by an interior sidewall that spans the inner diameter. The catheter may have an outer diameter, and the expandable portion may have an outer diameter coaxial therewith. The catheter may have a longitudinal axis, and the expandable portion may be a surface of revolution about the longitudinal axis. The expandable portion may be a balloon, which may be located at a distal end of the catheter. The first and second pumps may be located at a proximal end of the catheter. The proximal end of the catheter may be located in a sterile field.

The system may further comprise at least one switch for operating the first and second pumps. The first and second reservoirs may be removably attached to the first and second pumps. The at least one switch may operate the first pump at a steady flow rate, and the second pump at a variable flow rate. The system may further comprise at least one sensor configured to detect an actual measure in the interior kidney volume. The actual measure may include a pressure measure, and the at least one sensor may comprise a pressure sensor configured to detect the pressure measure. Either or both of the first and second pumps may be operable in response to the pressure measure. The pressure sensor may be attached to the distal end of the catheter. The actual measure may include a radiopacity measure, and the at least one sensor may comprise an imaging sensor configured to detect the radiopacity measure. Either or both of the first and second pumps may be operable in response to the radiopacity measure.

Another aspect is a method for irrigating an interior kidney volume in communication with a ureter. The method may comprise placing a distal end of a catheter into the interior kidney volume through a ureter, and occluding a portion of the ureter with an expandable portion of the catheter. An exit port may be formed in an exterior kidney surface. The method may comprise flowing a different fluid through either or both of at least two lumens in the catheter to supply a mixture in the interior kidney volume, and flushing a portion of the mixture out of the interior kidney volume through the exit port.

Aspects of this method may additionally and/or alternatively include one or more of the features set forth below. The expandable portion of the catheter may comprise a balloon, and the occluding step may further comprise expanding the balloon. Some aspects may further comprise a second catheter including a distal tip and at least one lumen, wherein the exit port may be located on the distal tip and in communication with the at least one lumen; in which case, the forming step may comprise inserting the distal tip into the interior kidney volume through an exterior kidney surface. At least one pump may be configured to flow the different fluids through either or both of the at least two lumens, and the flowing steps may comprise operating the at least one pump. The method may further comprise operating the at least one pump to maintain a constant volume of the mixture inside of the interior kidney volume.

Still another aspect is a method for irrigating a kidney. The method may comprise placing a distal end of a catheter into an interior kidney volume through a ureter, the catheter having a first lumen and a second lumen. A portion of the ureter may be occluded with an expandable portion of the catheter. A nephroscope may be inserted into the interior kidney volume to form an exit port. The method may further comprise flowing a contrasting agent through the first lumen and a dilating agent through the second lumen to supply a mixture of the contrasting and dilating agents in the interior kidney volume, and flushing a portion of the mixture out of the interior kidney volume through the exit port.

Aspects of this method may additionally and/or alternatively include one or more of the features set forth below. The placing step may further comprise inserting the distal end of the catheter into a urethra, and guiding the distal end into a urethra, through a bladder, through the ureter, and into the interior kidney volume. The nephroscope may have a rigid body with a distal tip. The exit port may be located on the distal tip, such that the inserting step comprises inserting the distal tip into the interior kidney volume through an exterior kidney surface. The expandable portion of the catheter may comprise a balloon, and the occluding step may further comprise expanding the balloon. This method may further comprise, prior to the occluding step, seating the expandable portion of the catheter at a ureteropelvic junction. Prior to the placing step, this method may comprise fragmenting a kidney stone in the interior kidney volume to form a plurality of stone fragments. A first pump may be operable to flow the dilating agent, and a second pump may be operable to flow the contrasting agent, such that the method comprises operating the first and second pumps to maintain a ratio of the dilating and contrasting agents in the interior kidney volume. This method may further comprise detecting, with at least one sensor, an actual measure in the interior kidney volume, establishing a target measure in the interior kidney volume, and operating the first and second pumps to obtain the target measure. The actual and target measures may be relative to the pressure in the interior kidney volume, or opacity of the mixture in the interior kidney volume.

It may be understood that both the foregoing summary and the following detailed descriptions are exemplary and explanatory only, neither being restrictive of the inventions claimed below.

BRIEF DESCRIPTION OF THE DRAWINGS

The accompanying drawings, which are incorporated in and constitute a part of this specification, illustrate exemplary aspects that, together with the written descriptions, serve to explain the principles of this disclosure.

DETAILED DESCRIPTION

The present disclosure is now described with reference to exemplary aspects of irrigation devices, methods, and systems. Some aspects are depicted and/or described with reference to a PCNL procedure, wherein irrigation techniques are used to flush a kidney with a mixture of different fluids. A plurality of kidney stone fragments may be flushed out of the kidney with the mixture. The plurality of stone fragments may be formed by fragmenting a kidney stone in advance. Any reference to a particular procedure (such as PCNL), targeted area of treatment (such as a kidney), technique (such as irrigation), or different fluids (such as dilating and contrasting agents) is provided for convenience and not intended to limit the present disclosure unless claimed. Accordingly, the concepts and novelty underlying each aspect may be utilized for any analogous device or method, medical or otherwise.

The directional terms "proximal" and "distal" are used to describe relative components and features of the present disclosure. Proximal refers to a position closer to the exterior of the body or a user, whereas distal refers to a position closer to the interior of the body or further away from the user. The term "elongated" as used herein refers to any object that is substantially longer in relation to its width, such as an object having a length that is at least two times longer than its width. Some elongated objects, for example, are axially extending in a proximal or distal direction along an axis. Unless claimed, these directional terms are provided for convenience and not intended to limit the present disclosure to a particular direction or orientation.

As used herein, the terms "comprises," "comprising," or like variation, are intended to cover a non-exclusive inclusion, such that a device or method that comprises a list of elements does not include only those elements, but may include other elements not expressly listed or inherent thereto. Unless stated otherwise, the term "exemplary" is used in the sense of "example," rather than "ideal."

Figure 1:
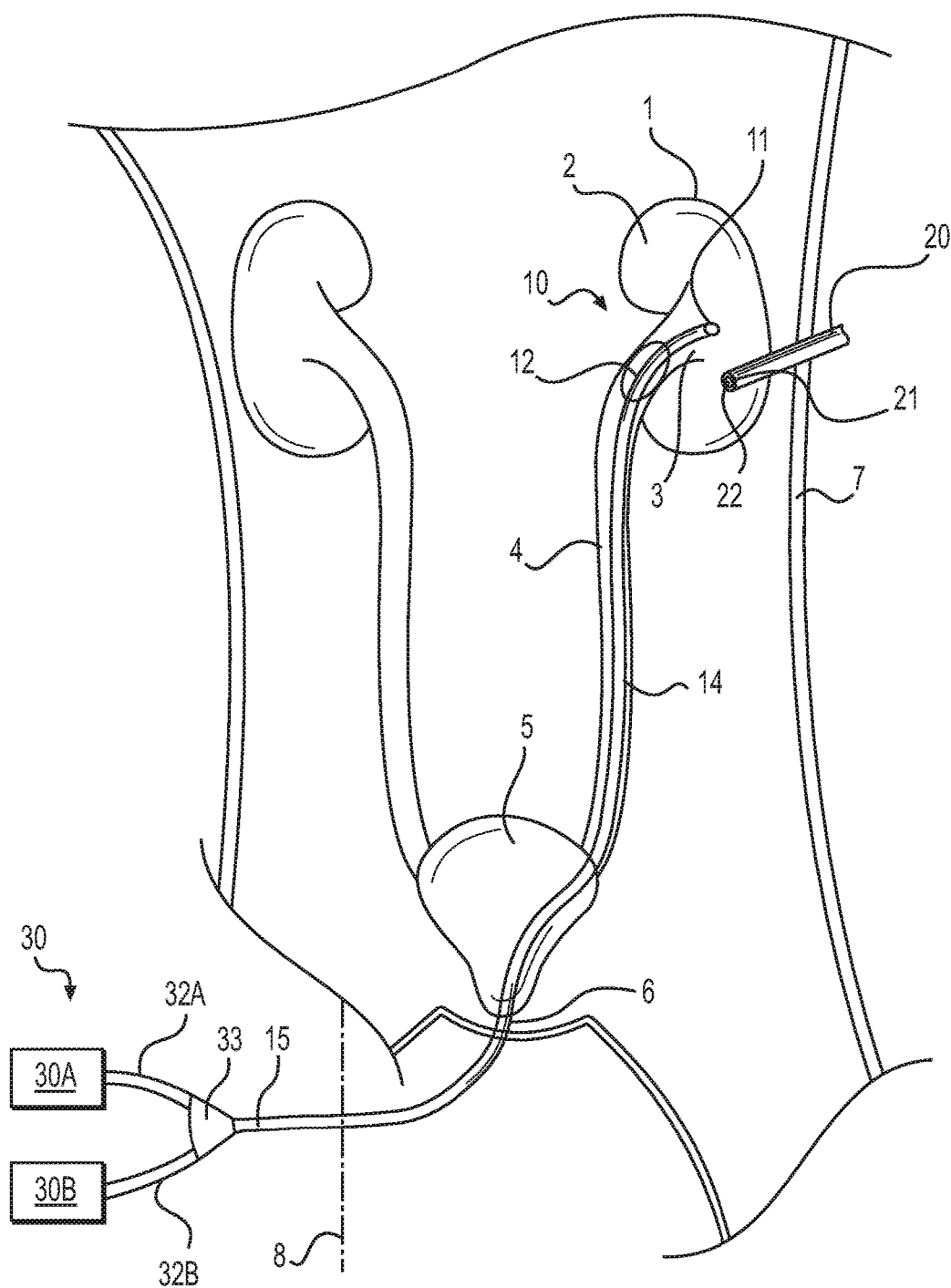
FIG. 1 depicts an exemplary irrigation system accordance with the present disclosure, wherein the system comprises a device and a fluid source.
Figure 2:
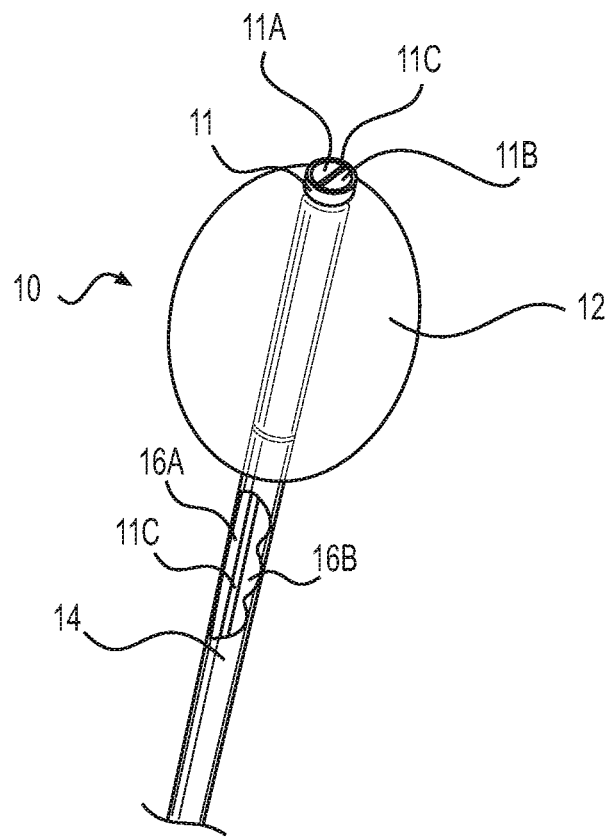
FIG. 2 is a view of an exemplary distal end of the device of FIG. 1.
Figure 3:
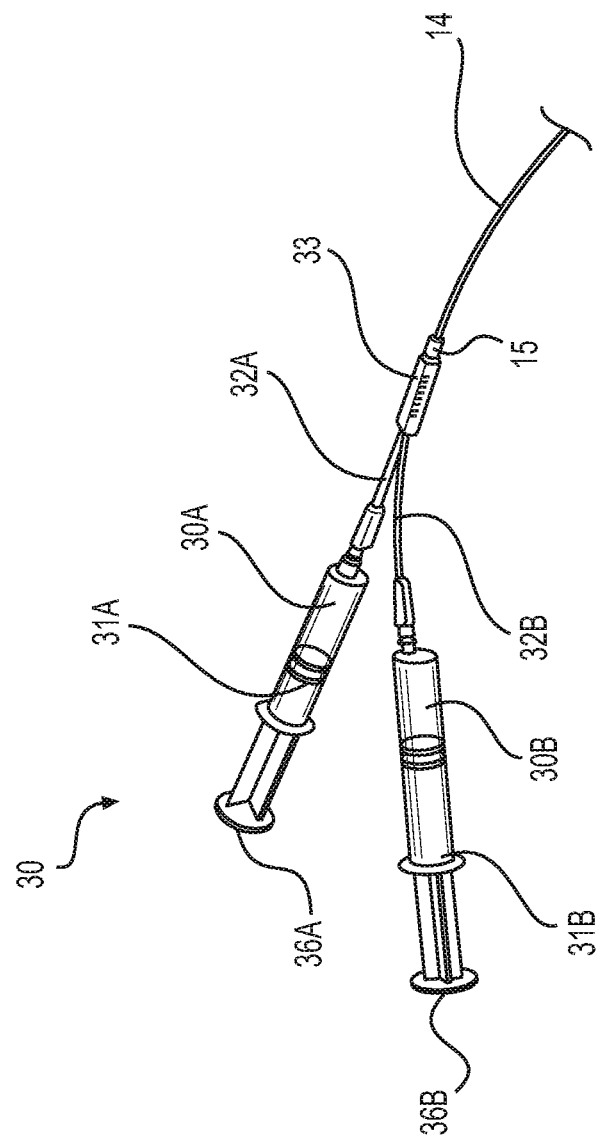
FIG. 3 is a view of an exemplary fluid source.
Figure 4A:
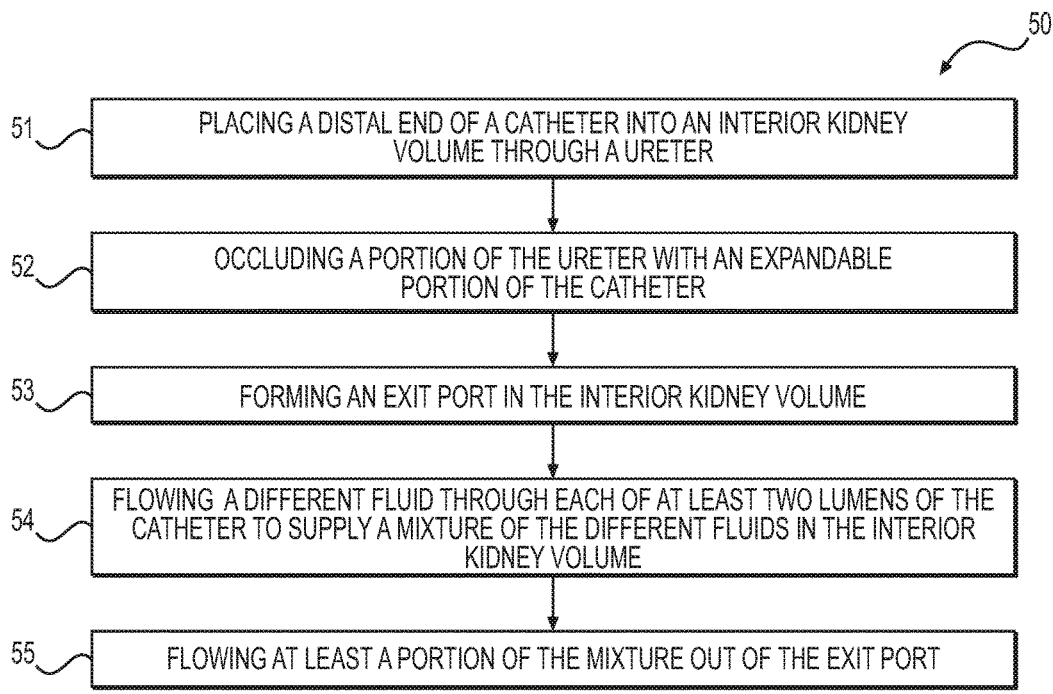
FIG. 4A depicts an exemplary method in accordance with the present disclosure.
Figure 4B:
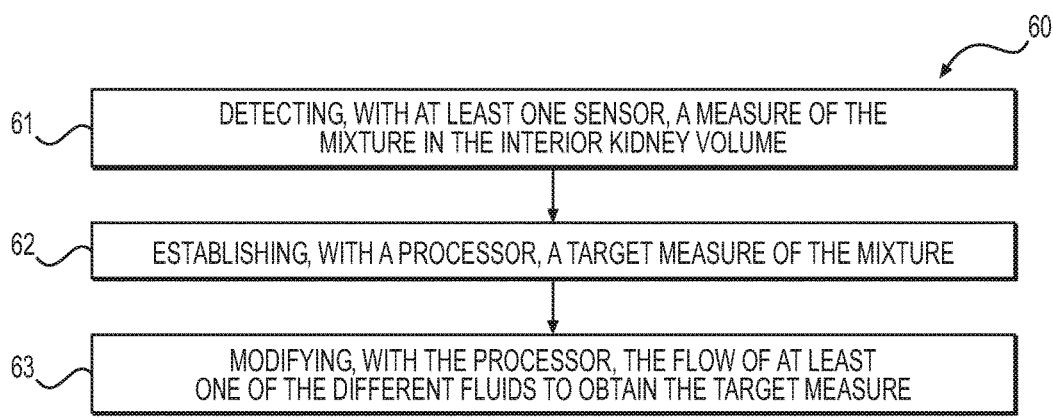
FIG. 4B depicts another exemplary method.

One aspect of the present disclosure is depicted in FIGS. 1-3 as a catheter 10 with a distal end 11, a proximal end 15, and an elongated catheter body 14 extending therebetween. As shown in FIG. 1, the distal end 11 of catheter 10 may be placed into an interior volume 2 of a kidney 1 using a retrograde approach, wherein distal end 11 is inserted into a urethra 6, advanced through a bladder 5, and then advanced through a ureter 4 for placement adjacent interior kidney volume 2. All, or at least an implanted portion, of catheter 10 may be made of a flexible biocompatible material, like silicone.

Distal end 11 of catheter 10 is configured to occlude a portion of ureter 4. In the aspect of FIGS. 1-2, an expandable portion 12 of elongated catheter body 14 is expanded to occlude ureter 4 by forming a pressure seal with the interior surfaces of ureter 4, thereby preventing any fluids from draining out of interior kidney volume 2 through ureter 4. Expandable portion 12 is illustrated in FIG. 2 as an occlusion balloon located adjacent distal end 11. An air supply line may be provided to inflate the balloon. This aspect of expandable portion 12 has an outer diameter coaxial with the outer diameter of catheter, and an outer surface formed as a surface of revolution about a longitudinal axis of distal end 11. Expandable portion 12 may either form a seal with ureter 4 or be seated in a uterepelvic junction 3.

Catheter 10 may have at least two lumens extending therethrough. The aspect of catheter 10 depicted in FIG. 2, for example, has a first lumen 16A and a second lumen 16B extending along the length of catheter 10 between distal end 11 and proximal end 15. Each lumen 16A, 16B is open to distal end 11 and proximal end 15. As illustrated, catheter 10 has an inner diameter that is divided by a sidewall 11C to define a first distal end opening 11A and a second distal end opening 11B. Although not required, openings 11A and 11B may have a semi-circular shape at distal end 11.

Proximal end 15 of catheter 10 is attached to a fluid source 30. As shown in FIG. 1, fluid source 30 includes a first reservoir 30A attached to a first supply line 32A and a second reservoir 30B attached to a second supply line 32B. Each of supply lines 32A and 32B are attached to, respectively, one of first and second lumens 16A and 16B by a manifold 33. One aspect of fluid source 30 is depicted in FIG. 3 as a pair of syringes 31A and 31B, each housing one of the reservoirs 30A or 30B. Each syringe 31A and 31B has a plunger 36A or 36B configured to flow a fluid from reservoirs 30A, 30B, through supply lines 32A, 32B, and into lumens 16A, 16B, for distribution in interior kidney volume 2. Each plunger 36A and 36B serves as a manually operated pump in this aspect. A surgical drape 8 is depicted in FIG. 3. Proximal end 15 of catheter 10 and fluid source 30 are located outside a sterile field defined by drape 8.

Figure 6:
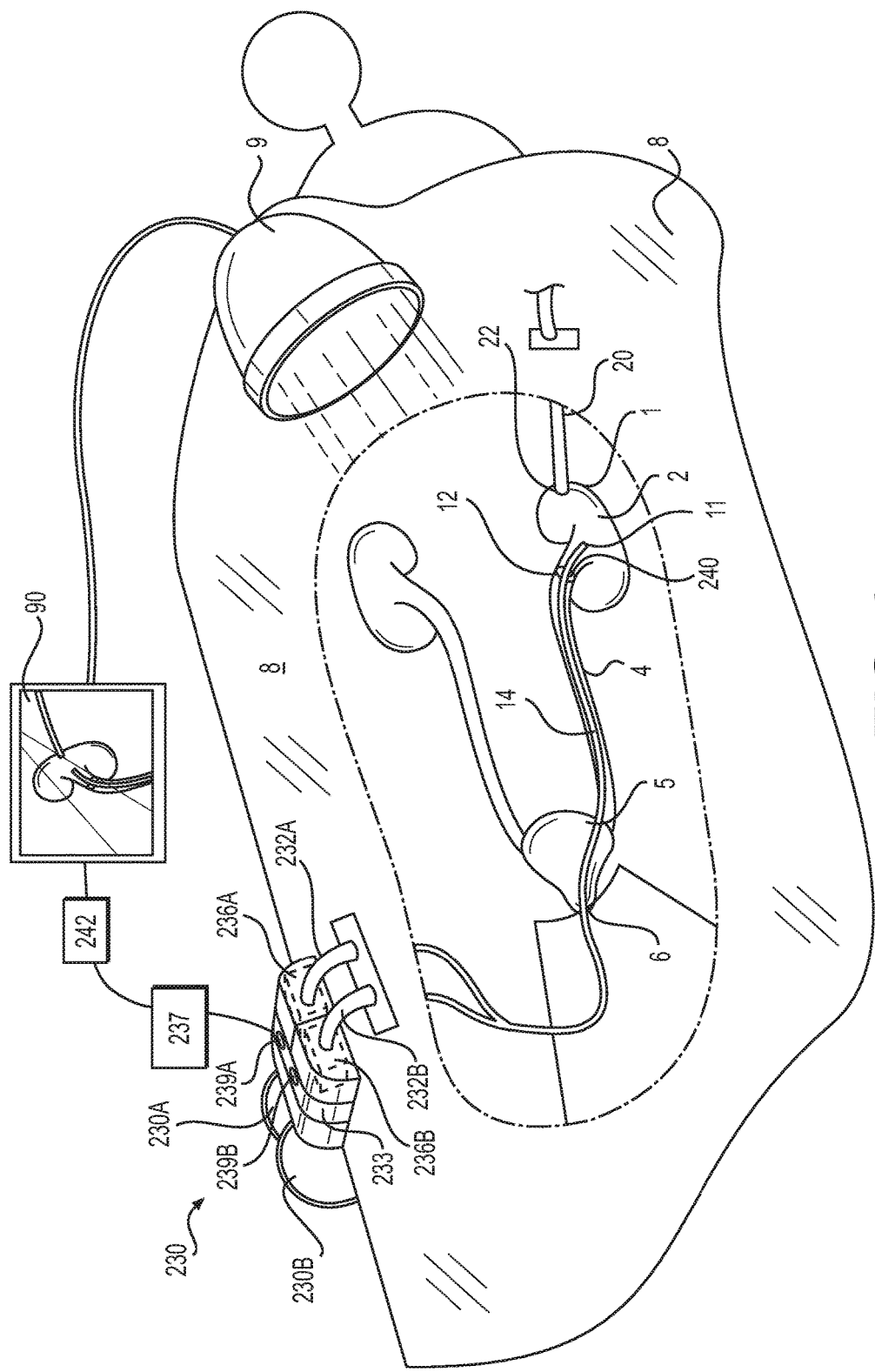
FIG. 6 depicts yet another exemplary fluid source

Each reservoir 30A and 30B is configured to hold a fluid. In FIG. 3, for example, first reservoir 30A holds a first fluid, such as a dilating agent like saline, while second reservoir 30B holds a second fluid, such as a contrasting agent like iodine or barium. The exterior surface of kidney 1 (FIG. 1) is a tough, multi-layered tissue impermeable to the first and second fluids. Plungers 36A and 36B are operable to supply a mixture of the first and second fluids in interior kidney volume 2, which acts like a pressure vessel to contain the mixture. The mixture may be supplied to achieve certain benefits. In some aspects, the mixture is supplied to flush contaminants out of interior kidney volume 2 through an exit port 22 formed in kidney 1 (FIG. 1). In other aspects, the mixture is supplied to enhance the visibility of interior kidney volume 2 when viewed through a medical imaging device 9 (FIG. 6). For example, the ratio of contrasting and dilating agents in the mixture may be optimized by operating plungers 36A and 36B to achieve a targeted radiopacity measure in interior kidney volume 2, thereby enhancing the visibility of each calyx in kidney 1 when viewed with imaging device 9 (FIG. 6).

Plungers 36A and 36B are operable to flush at least portion of the mixture out of exit port 22. As shown in FIG. 1, exit port 22 is formed in interior kidney volume 2 by placing a distal tip 21 of a second catheter 20 through the exterior kidney surface. Distal tip 21 may be placed in interior kidney volume 2 using an antegrade approach, wherein distal tip 21 is inserted through an exterior skin 7 of a body and then passed through various bodily tissues, including the exterior kidneys surface, for placement in interior kidney volume 2.

Numerous methods for using catheter 10 and fluid source 30 are now described with reference to FIGS. 1-4. One example is a method 50 (FIG. 4A) for irrigating interior kidney volume 2. Method 50 may be performed after an initial step of fragmenting a kidney stone in the interior kidney volume to form a plurality of stone fragments. Any fragmentation technique may be used, including those based on a disruptive energy such as that applied by sound waves, lasers, etc.

An exemplary method 50 comprises a step 51 of placing the distal end 11 of catheter 10 adjacent interior kidney volume 2 through ureter 4. Step 51 may be performed using a retrograde approach, wherein step 51 further comprises a step for inserting distal end 11 into urethra 6; and a step for guiding distal end 11 through bladder 5 and ureter 4 for placement adjacent interior volume 2. Another step 52 comprises occluding a portion of ureter 4 with distal end 11. As described above, catheter 10 may have an expandable portion 12, such that step 52 further comprises expanding portion 12. If portion 12 is a balloon, then step 52 may further comprise inflating the balloon. In some aspects, step 52 may further comprise seating expandable portion 12 at ureterojunction 3 by, for example, applying a proximally-directed force to elongated catheter body 14.

In this method 50, another step 53 comprises forming exit port 22 by inserting the distal tip 21 of second catheter 20 through the exterior surface of kidney 1 (FIG. 1). Second catheter 20 may be a nephroscope with a distal tip, wherein step 53 comprises inserting the tip of the nephroscope into interior kidney volume 2 through exterior skin 7 and the exterior kidney surface using an antegrade approach. In some aspects, step 53 may be preceded by a step of inserting a distal end of a sheath through an opening in the exterior surface of kidney 1, and dilating the sheath to seal the exterior surfaces of the tract against the interior surface of the opening. Accordingly, step 53 may further comprise inserting the nephroscope into kidney 1 through a lumen of the tract. A grommet, o-ring, or like sealing element may be placed around the exterior surfaces of the nephroscope to prevent unwanted fluid flow.

Method 50 further comprises a step 54 of flowing a different fluid through either or both of at least two lumens 16A, 16B of catheter 10 to supply a mixture in interior kidney volume 2; and a step 55 of flushing at least a portion of the mixture out of exit port 22. Each of steps 54 and 55 may be performed by operating plungers 36A and 36B. For example, each step 54, 55 may further comprise a step for depressing either or both of plungers 36A or 36B by a first amount to flow either or both of the different fluids from reservoirs 30A, 30B, through supply lines 32A, 32B, and into lumens 16A, 16B, to supply the mixture in interior kidney volume 2. Method 50 may comprise another step for depressing plungers 36A, 36B by a second amount to flush a portion of the mixture out of exit port 22. For example, plungers 36A and 36B may be depressed to pressurize the mixture in interior kidney volume 2 until a portion of the mixture flows out of exit port 22.

Figure 5:
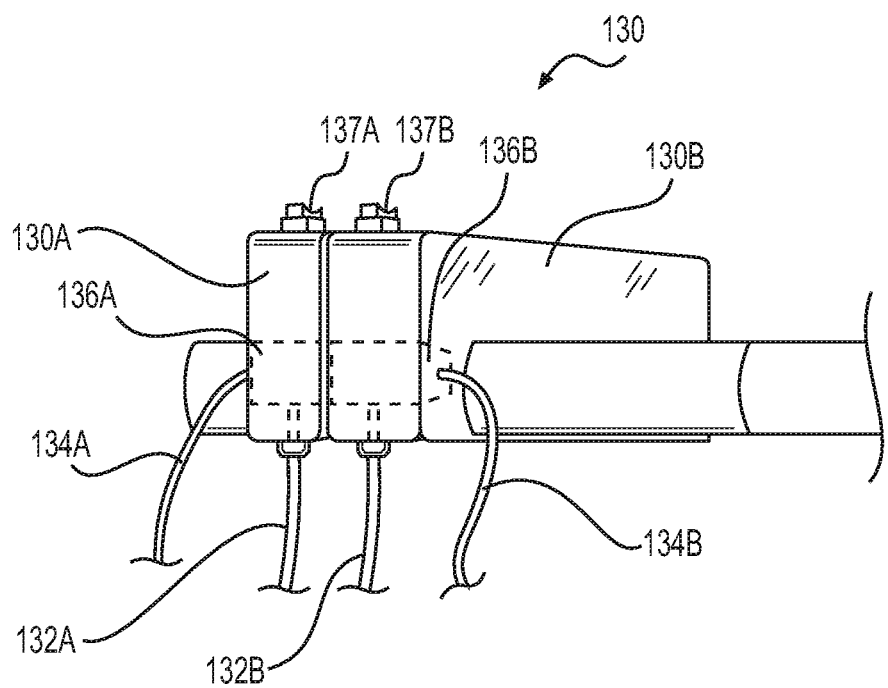
FIG. 5 depicts another exemplary fluid source.

Another aspect of the present disclosure is shown in FIG. 5 and now described with reference to catheter 10, exit port 20, and a fluid source 130, which is an alternate aspect of fluid source 30. Catheter 10 is described above. Source 130 has a first reservoir 130A and second reservoir 130B, each being configured to hold a fluid. Reservoir 130A may hold a first fluid, such as the dilating agent, while second reservoir 130B holds a second fluid, such as the contrasting agent.

In contrast to above, fluid source 130 has a first pump 136A and a second pump 136B. Pumps 136A, 136B may comprise any known pumping technology. As shown in FIG. 5, for example, each pump 136A and 136B is an electric pump configured to pull the first and second fluids from reservoirs 130A and 130B and into interior kidney volume 2 through one of a first supply line 132A and a second supply line 132B. A power cable 134A or 134B provides electricity to each pump. First and second pumps 136A and 136B may be operated by one or more control switches. For example, first pump 136A of FIG. 5 is operated by moving a toggle switch 137A into an "on" position to flow the first fluid at a constant flow, thereby ensuring that kidney 1 will remain dilated until toggle switch 137A is moved into an "off" position. Second pump 136B of FIG. 5 is operated by moving a biased switch 137B into an "on" position to flow the second fluid, thereby ensuring that the mixture will be increasingly radiopaque until biased switch 137B is released. Accordingly, pumps 136A and 136B, like plungers 36A and 36B, are operable to supply a mixture of the contrasting and dilating agents in interior kidney volume 2, and flush one or more contaminants out of exit port 22 (FIG. 1) with a portion of the mixture.

Aspects of method 50 may be used with fluid source 130. For example, because pumps 136A and 136B perform the function of plungers 36A and 36B, steps 54 and 55 may further comprise activating either or both of switches 137A and 137B to flow either or both of the first and second fluids to supply a mixture to interior kidney volume 3 and flush a portion of the mixture out of exit port 22. A further step may comprise activating switch 137B, for example, to adjust the radiopacity of the mixture. Another step may comprise activating either or both of switches 137A, 137B to maintain a targeted ratio or amount of the dilating and contrasting agents in interior kidney volume 2. In some aspects, the targeted ratio of dilating to contrasting agents may be maintained at a ratio of approximately 1:1 to facilitate placement of first and/or second catheter 10, 20, as described above, and then gradually changed to a ratio of approximately 1:0 for another step of the procedure. Any relative values may be used, and any such values may be varied, as needed, by activating either or both of switches 137A and 137B.

Figure 7:
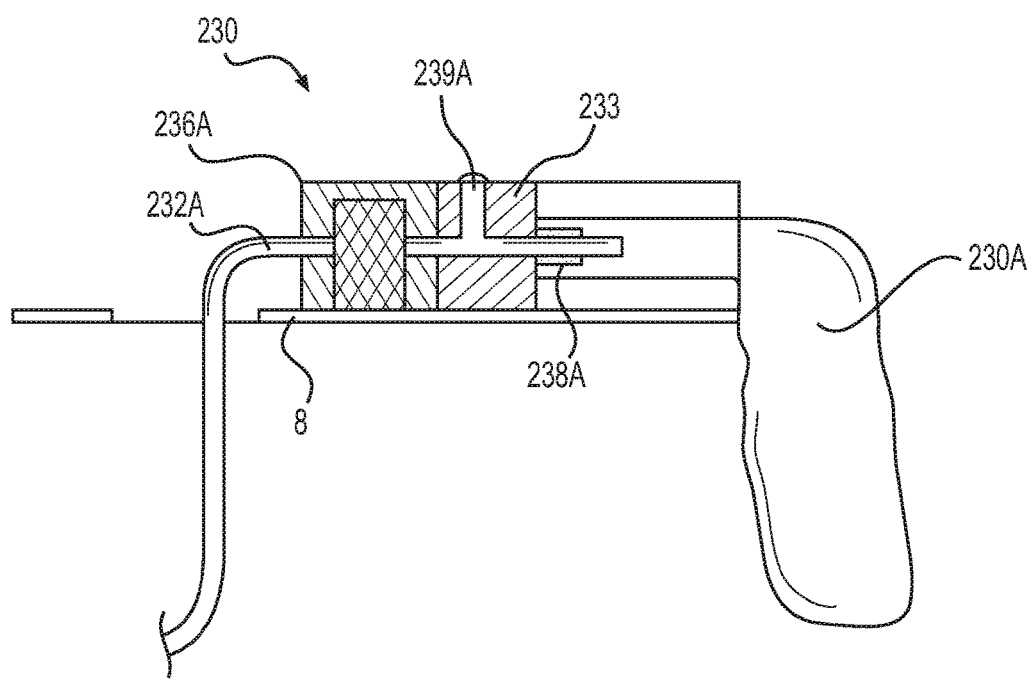
FIG. 7 is a section view of the fluid source of FIG. 6.

Another aspect of the present disclosure is now described with reference to catheter 10 and a fluid source 230, which is another alternate fluid source 30. Catheter 10 is described above. An exemplary aspect of fluid source 230 is depicted in FIGS. 6 and 7 as including a first reservoir 230A, a second reservoir 230B, and a pump manifold 233. Source 230 has a first pump 236A and a second pump 236B, either of which may comprise any known pumping technology. As shown in FIG. 7, reservoir 230A, for example, is removably attached to an engagement portion 238A of manifold 233. Reservoir 230B may be identically structured. A set of ports 239A and 239B are illustrated in FIGS. 6 and 7 as extending through manifold 233 to allow another fluid to be introduced into the mixture. The respective first and second fluids flow from pumps 236A and 236B and into interior kidney volume 2 through a first supply line 232A and a second supply line 232B. Accordingly, first and second reservoirs 230A and 230B are removably attached to first and second pumps 236A and 236B.

Fluid source 230 comprises at least one sensor configured to detect a measure in interior kidney volume 2. A first sensor 240 and a second sensor 242 are depicted in FIG. 6. Any sensing technology, or combination of such technologies, may be used. As shown, first sensor 240 detects a pressure measure in interior kidney volume 2. Sensor 240 may, for example, be a strain gauge attached to distal end 11 of catheter 10. Second sensor 242 of FIG. 6 detects a radiopacity measure in volume 2. Sensor 242 may, for example, be an active-pixel sensor located outside of the sterile field and configured detect the measure by sampling pixel color and contrast in an image 90 taken by an imaging machine 9 (FIG. 6).

First and second pumps 236A and 236B of FIG. 6 are electronic pumps operated by a processor 237, which may be any known processing device, such as a computer. First and second sensors 240 and 242 communicate with processor 237 using a wired or wireless connection to provide for automated control of first and second pumps 236A and 238B. For example, either or both of first and second pumps 236A and 236B may be operated by processor 237 in response to first and/or second sensors 240 and 242. To avoid unwanted backflow or over-dilating kidney 1, a pressure safeguard may be realized by operating either or both of first and second pumps 236A and 236B in response to the pressure measure detected by sensor 240. For example, an upper limit to fluid pressure in interior kidney volume 2 may be relative to pyelovenous backflow, which occurs at approximately 30 mm Hg (or 0.58 psi) or greater; pyelotubular backflow, which occurs at approximately 40 mm Hg (or 0.77 psi) or greater; pyelolymphatic backflow, which occurs at approximately 60 mm Hg (or 1.16 psi) or greater; or forniceal rupture, which occurs at approximately 100 mm Hg (or 1.93 psi) or greater. Either or both of pumps 236A and 236B may be operated in response to the pressure measure obtained by first sensor 240 to ensure that any one or more of these upper limits are not exceeded. In some aspects, either or both of pumps 236A and 236B may be operated to maintain an operating pressure of approximately 0 mmHg to approximately 60 mmHg (or approximately 0 psi to approximately 1.16 psi) in interior kidney volume 2.

Either or both of first and second pumps 236A and 236B may also be operated to flush kidney 1 with the mixture. Thus, to continue this example, a targeted ratio or amount of fluids in volume 2 may be maintained, even if kidney 1 is continually flushed, by operating either or both of the first and second pumps 236A and 236B in response to the radiopacity measure detected by second sensor 242. For example, at least second pump 236B may be operated in response to sensor 242 to maintain the targeted ratio or amount of contrasting and dilating agents in the mixture, even as a portion of the mixture is continuously flushed out of exit port 22. The targeted ratio may also be varied, such that either or both of pumps 236A and 236B may be operated in response to sensor 242 so as to maintain a first targeted ratio during an initial part of a procedure and a second targeted ratio during a subsequent part of a procedure. For example, a first ratio of approximately 1:1 for the dilating and contrasting agents may be maintained to facilitate placement of first or second catheters 10, 20, whilst a second ratio of 1:0, dilating to contrasting agent, may be maintained thereafter. Any relative values may be used. This transition may be rendered in a gradual or abrupt manner by operation of either or both of pumps 236A and 236B.

Similar to above, aspects of method 50 may be used with fluid source 230. For example, pumps 236A and 236B may be operated in accordance with steps 54 and 55 by using processor 237 to supply the mixture and flush a portion of the mixture out of an exit port 22 formed in interior kidney volume 2. Step 54 may be implemented with method 60 as provided in FIG. 4B. The placing, occluding, and forming steps of method 60 may be performed as discussed above in method 50. Method 60 comprises a step 61 for detecting, with at least one sensor, a measure in interior kidney volume 2, such as the pressure or radiopacity measures described above with reference to first and second sensors 240 and/or 242. Another method step 62 comprises establishing, with processor 237, a target measure in interior kidney volume 2. For example, a target flow rate of the dilating fluid may be established to regulate a pressure measure in volume 2. Alternatively, a target ratio or amount of dilating and contrasting agents may be established to maintain a radiopacity measure. Another method step 63 comprises modifying, with processor 237, the flow of either of the dilating or contrasting agent to obtain the target measure, for example, by operating either of the first and second pumps 236A and 236B.

Each device, method, and system has been described as operable to supply a mixture of different fluids in interior kidney volume 2, and flush a portion of the mixture out of volume 2. This disclosure allows the mixture to be used in an irrigation technique that is both compatible with a retrograde approach and provides a means for enhancing the visibility of interior kidney volume 2. Moreover, by flowing the fluids as described, the contrast of the mixture may be modified to any particular level, and maintained indefinitely at that level, even if kidney 1 is flushed continually. Numerous alternative aspects are now described. Each of these alternative aspects may enhance the performance of the any device, method, or system described herein. Any feature of any alternative aspect described herein may be combined with any other feature described herein, each possible variant being part of the present disclosure.

Distal end 11 is described as having an expandable portion 12 configured to occlude ureter 4. In some aspects, portion 12 is a balloon. Expandable portion 12 may assume any shape, regular or irregular, symmetrical or asymmetrical. For example, portion 12 may be irregularly shaped to seal a particular ureteropelvic junction 3, or formed of a flexible material that naturally form fits to the contours of ureter 4 or junction 3 when expanded. Catheter 10 may have a plurality of expandable portions 12, each portion being spaced apart on elongated catheter body 14 to seal ureter 4 at a plurality of locations. Although described as being expanded by air, portion 12 may alternatively be filled by a fluid. For example, either of lumens 16A, 16B might have a port that opens into portion 12, allowing it to be expanded by either the first or second fluid.

Catheter 10 of FIGS. 1-3 has two lumens 16A and 16B for delivery of two different fluids, although any number of lumens may be provided. For example, if expandable portion 12 of catheter 10 is a balloon, then the aforementioned air supply line may be one or more additional lumens that open into expandable portion 12 of catheter 10. An exit lumen may be provided with a pressure relieve valve, thus providing a further safeguard against over-dilation of kidney 1. Lumens 16A and 16B are depicted in FIG. 2 as being approximately equal in size, but may be sized differently. Each lumen has also been described as having an opening 11A or 11B with a semi-circular shape. These openings may assume any shape. For example, a nozzle may be provided in one or both openings 11A, 11B to vary the pressure of any fluid delivered therethrough.

First and second fluids have been described as, respectively, a dilating agent and a contrasting agent. Any fluid types may be used. For example, one of the fluids may include a medicating agent, such as an anti-inflammatory, that is circulated through kidney 1 during a procedure. Other fluid types may be circulated to further dissolve the plurality of kidney stone fragments, promote the formation of a seal between expandable portion 12 and ureter 4, or provide like benefits. These additional fluids may be introduced through manifold 33, passed through second catheter 20 (FIG. 1), injected into ports 239A and 239B (FIG. 7), or otherwise provided. Fluid sources 30, 130, and 230 have each been described as having two pumps (36A-B, 136A-B, or 236A-B), and two reservoirs (32A-B, 132A-B, or 232A-B) for the purpose of flowing the first and second fluids. Any number of pumps or reservoirs may be provided to realize any of these alternative aspects.

Any type of switching and/or sensing technologies may be incorporated into any aspect of fluid sources 30, 130, or 230 to aid in circulating the mixture, maintaining a characteristic of the mixture, or flushing kidney 1. Processor 237 may be utilized to automate any of these functions of these fluid sources. For example, pumps 236A and 236B may be operated, with processor 237, according to automated control sequence responsive to a signal generated by either or both of sensors 240 and 242. Given the variety of sensing technologies, it should be appreciated that pumps 236A and 236B may be operated by any sensing technology to deliver a corresponding variety of benefits. For example, one or more additional sensors may be configured to detect a measure of blood in the fluid mixture, such that either or both of pumps 236A or 236B may be operated in response to the one or more additional sensors to automatically notify the physician if/when a safeguard is tripped, responsively reduce the pressure or increase the opacity of the mixture in interior kidney volume 2, or introduce a medicating agent into the mixture.

Any of the method steps described above with reference to exemplary methods 50 and 60 may be modified to accommodate the structure of any of these alternative aspects. For example, method 50 may be modified for use with an type of fluids, through any number of lumens, etc.; and method 60 may be modified for use with any type of sensor, switch, processor, or the like. In either instance, methods 50 and 60 may be further modified supply the mixture in interior kidney volume 2 and flush one or more contaminants out of interior volume 2.

While principles of the present disclosure are described herein with reference to illustrative aspects for particular applications, the disclosure is not limited thereto. Those having ordinary skill in the art and access to the teachings provided herein will recognize additional modifications, applications, aspects, and substitution of equivalents all fall in the scope of the aspects described herein. Accordingly, the present disclosure is not to be considered as limited by the foregoing description.

The invention claimed is:

1. A method for irrigating a kidney, the method comprising:
    placing a distal end of a catheter adjacent an interior kidney volume through a ureter;
    occluding a portion of the ureter with an expandable portion of the catheter;
    forming an exit port;
    flowing a different fluid through each of at least two lumens in the catheter to supply a mixture in the interior kidney volume;
    flushing a portion of the mixture out of the interior kidney volume through the exit port;
    detecting, with at least one sensor, an actual volume in the interior kidney volume;
    establishing a target volume in the interior kidney volume; and
    delivering the different fluids through each of the at least two lumens in the catheter to obtain the target volume in the interior of the kidney volume.

2. The method of claim 1, wherein the expandable portion of the catheter comprises a balloon, and the occluding step further comprises expanding the balloon.

3. The method of claim 1, further comprising a second catheter including a distal tip and at least one lumen, wherein the exit port is located on the distal tip and in communication with the at least one lumen, and the forming step comprises inserting the distal tip into the interior kidney volume through the exterior kidney surface.

4. The method of claim 1, further comprising at least one pump configured to flow the different fluids through each of the at least two lumens, wherein the flowing step comprises operating the at least one pump.

5. The method of claim 4, further comprising operating the at least one pump to maintain a constant volume of the mixture inside of the interior kidney volume.

6. The method of claim 1, wherein the delivery of the different fluids includes activating different pumps to deliver each different fluid, and further including:
    operating the different pumps to maintain a ratio of the different fluids in the interior kidney volume.

7. A method for irrigating an interior kidney volume, the method comprising:
    placing a distal end of a catheter adjacent the interior kidney volume through a ureter, the catheter having a first lumen and a second lumen;
    occluding a portion of the ureter with an expandable portion of the catheter;
    inserting a nephroscope into the interior kidney volume to form an exit port;

flowing a contrasting agent through the first lumen and a dilating agent through the second lumen to supply a mixture of the contrasting and dilating agents in the interior kidney volume, wherein flowing the contrasting agent and the dilating agent includes operating a first pump operable to flow the dilating agent, operating a second pump operable to flow the contrasting agent, and operating the first and second pumps to maintain a ratio of the dilating and contrasting agents in the interior kidney volume;

flushing a portion of the mixture out of the interior kidney volume through the exit port;

detecting, with at least one sensor, an actual measure in the interior kidney volume;

establishing a target measure in the interior kidney volume; and operating the first and second pumps to obtain the target measure in the interior kidney volume.

8. The method of claim 7, wherein the placing step further comprises:

inserting the distal end of the catheter into a urethra; and guiding the distal end into a urethra, through a bladder, and through the ureter.

9. The method of claim 7, wherein the nephroscope has a rigid body with a distal tip, the exit port is located on the distal tip, and the inserting step comprises inserting the distal tip through an exterior kidney surface, and wherein the expandable portion of the catheter comprises a balloon, and the occluding step further comprises expanding the balloon.

10. The method of claim 9, further comprising, prior to the occluding step, seating the expandable portion of the catheter at a ureteropelvic junction.

11. The method of claim 7, further comprising, prior to the placing step, fragmenting a kidney stone in the interior kidney volume to form a plurality of stone fragments.

12. The method of claim 7, wherein the actual and target measures are relative to at least the pressure in the interior kidney volume.

* * * * *